United States Patent [19]

Imanaka et al.

[11] Patent Number: 5,344,913

[45] Date of Patent: Sep. 6, 1994

[54] BIOSURFACTANT CYCLOPEPTIDE COMPOUND PRODUCED BY CULTURING A SPECIFIC ARTHROBACTER MICROORGANISM

[75] Inventors: Tadayuki Imanaka, Suita; Shoji Sakurai, Shizuoka, both of Japan

[73] Assignee: Nikko Bio Technica Co., Ltd., Shizuoka, Japan

[21] Appl. No.: 136,261

[22] Filed: Oct. 15, 1993

[30] Foreign Application Priority Data

Oct. 15, 1992 [JP] Japan .................................. 4-303131
Jul. 9, 1993 [JP] Japan .................................. 5-194215

[51] Int. Cl.$^5$ .................... C12P 21/04; C12R 1/06; A61K 37/02
[52] U.S. Cl. ................................ 530/321; 435/71.2; 435/830; 530/317
[58] Field of Search ............... 530/317, 321; 435/71.2, 435/830

[56] References Cited

U.S. PATENT DOCUMENTS 4,918,161  4/1990  Steinbrink .......................... 530/300

OTHER PUBLICATIONS

CA118(21):209163(e) (1993) Nakagawa et al "FEMs Microbioc Lett" 108(1) 99–102.
CA116(21) 210854w (1992) Matsuyama et al "J. Bacteriol" 174(6) 1769–76.

*Primary Examiner*—Herbert J. Lilling
*Attorney, Agent, or Firm*—Bacon & Thomas

[57] ABSTRACT

A novel biosurfactant having a high surface activity, as well as a microorganism producing the surfactant is disclosed. The biosurfactant according to the present invention is represented by the formula [I].

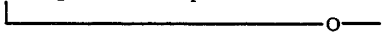

The present invention also provides Arthrobacter sp. No. 38 (FERM BP-4435) which produces the biosurfactant of the formula [I].

2 Claims, 6 Drawing Sheets

BIOSURFACTANT CYCLOPEPTIDE COMPOUND PRODUCED BY CULTURING A SPECIFIC ARTHROBACTER MICROORGANISM

BACKGROUND OF THE INVENTION

I. Field of the Invention

This invention relates to a novel compound having a surface activity, a process for producing the same and to a novel microorganism producing the same.

II. Description of the Related Art

Biosurfactants (hereinafter also referred to as "BS") which are originated from living organisms have structures and functions which are different from those of synthetic surfactants. Since the skeletons of most of known biosurfactants are made of lipopeptides or glycolipids, they are detergents highly bio-degradable. On the other hand, they inhibit growth of some bacteria. Further, it is expected that third recovery of petroleum may be attained by culturing BS-producing bacteria in underground petroleum layers.

Although various biosurfactants are known including surfactin (Arima K. et al., Biochemical and Biophysical Research Communications 31, 488-494 (1968)), it is desired that a biosurfactant having a higher surface activity than those of the known biosurfactants be provided.

SUMMARY OF THE INVENTION

Accordingly, an object of the present invention is to provide a novel compound having a high surface activity, which is produced by a microorganism, as well as to provide a production process thereof and a novel microorganism producing the compound.

The present inventors intensively studied to discover a novel bacterium belonging to genus Arthrobacter and that this novel bacterium produces a novel compound having a high surface activity. The present inventors succeeded in isolating the novel compound and determining the chemical structure thereof, thereby completing the present invention.

That is, the present invention provides a compound represented by the formula [I].

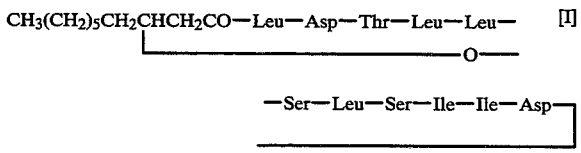

The present invention also provides a process for producing the above-described compound of the present invention, comprising the steps of culturing a bacterium belonging to genus Arthrobacter which produces the compound according to the present invention in conditions which allow production of said compound; and recovering the compound from the culture.

The present invention still further provides Arthrobacter sp. No. 38 (FERM BP-4435).

By the present invention, a novel biosurfactant having a high surface activity, a production process thereof and a novel microorganism which produces the biosurfactant were provided. Since the compound according to the present invention has higher surface activity per one molecule than any known biosurfactant, it is expected that the biosurfactant according to the present invention will be used as a strong detergent which is highly bio-degradable.

DETAILED DESCRIPTION OF THE PREFERRED EMBODIMENTS

Figure 1:
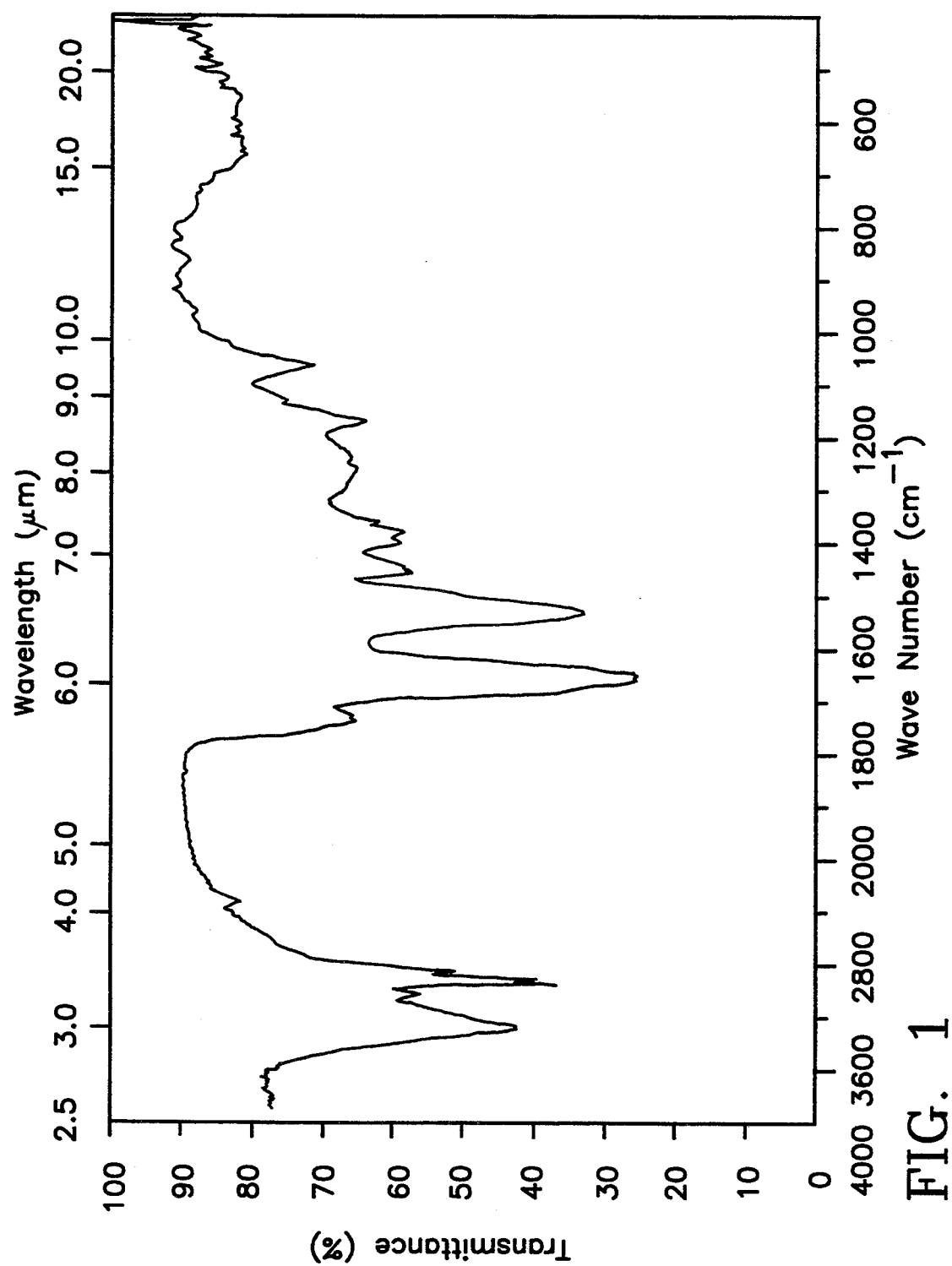
FIG. 1 shows an infrared absorption spectrum of the compound according to the present invention.

Arthrobacter sp. No. 38 (hereinafter also referred to as "No. 38 strain") was isolated from soil near Sagara petroleum field in Shizuoka, Japan as a strain which forms the largest emulsified halo on L agar medium on which oil was applied, that is, as a biosurfactantproducing strain. No. 38 strain has the following mycological properties:

(1) Growing Temperature: 25-37° C.
(2) Optimum Temperature: 30° C.
(3) Strictly aerobic Gram-positive bacterium
(4) Spore Formation: none
(5) Typical rod-coccus cycle is observed during culture.
(6) It has mobility.
(7) Acid-fast Staining: negative
(8) Its cell wall contains lysine.

From the above-described mycological properties, No. 38 strain was identified as belonging to genus Arthrobacter. No. 38 strain was deposited with National Institute of Bioscience and Human-Technology (formerly Fermentation Research Institute), Agency of Industrial Science and Technology, at 1-3, Higashi 1 chome, Tsukuba-shi, Ibaraki-ken 305, Japan, on Oct. 14, 1992 and the deposition was converted to international deposition under the Budapest Treaty on Oct. 5, 1993. The accession number of the international deposition is FERM BP-4435.

The novel compound according to the present invention has the chemical structure shown by the abovedescribed formula [I]. This compound (hereinafter also referred to as "BS-38") is produced by a microorganism and has a surface activity, so that the compound is a biosurfactant. Thus, the compound has a use as a surface active agent.

As described in detail in the examples below, BS-38 has higher surface activity per one molecule than the surfactin which has the highest surface activity of all the conventional biosurfactants.

BS-38 may be obtained by culturing No. 38 strain and recovering the compound from the culture supernatant. The recovery may be attained by a conventional method employing chromatography and/or ultrafiltration. A specific example of recovering BS-38 is described in Examples below. No. 38 strain may be cultured, for example, in L medium, preferably at 30° C. By culturing No. 38 strain in L medium at 30° C. for 24 hours, BS-38 is produced in the culture supernatant. The amount of the BS-38 produced in the culture supernatant is about 30 mg per 1 liter of culture liquid.

The present invention will now be described by way of examples thereof. It should be noted that the examples are presented for the illustration purpose only and should not be interpreted in any restrictive way.

EXAMPLE 1

Isolation of No. 38 Strain

No. 38 strain was isolated by the following method: The soil (about 1 g) near Sagara petroleum field in Shizuoka, Japan is suspended in sterilized water (10 ml). Petroleum (40 μl) produced in Sagara petroleum field is preliminarily applied to L agar medium in a petri dish to obtain an oil plate. The suspension of the soil (0.1 ml) is spread on the thus prepared oil plate and the oil plate is incubated at 28° C. or 37° C. for 2 days to 1 week. The emerged colonies are then observed. Those which formed emulsified halos around the colony were isolated as biosurfactant-producing bacteria. No. 38 strain was isolated from the colony which formed the largest halo.

EXAMPLE 2

Isolation of BS-38

No. 38 strain was cultured in L medium at 30° C. for 24 hours. BS-38 was isolated from the culture supernatant by the following method: The culture supernatant was about 10-fold concentrated by ultrafiltration (fractionation molecular weight: 10,000) and CaCl₂ and HCl were added to the resultant to concentrations of 50 mM and 10 mM, respectively. The resultant was left to stand at room temperature for 6 hours and the formed precipitates were recovered by centrifugation. The precipitates were neutralized with aqueous NaOH solution to dissolve the precipitates. From the resultant, lipid fraction was extracted with hexane or ethyl acetate and the extract was purified by silica gel column and octadecyl column. The conditions of the chromatography were as follows: Sample was dissolved with chloroform/methanol (1:1) and applied on the Silica gel C-200 column (φ 30 mm×500 mm). Active fraction was eluted with chloroform/methanol/water (65:25:4), whereas hydrophilic substances remained in the column. After drying, the sample was dissolved with 50% acetonitrile and further purified by Octadecyl-4PW HPLC column (Tosoh Corp., Tokyo, Japan). Elution was performed by using a linear gradient of 10% acetonitrile (0.1% TFA) and 90% acetonitrile (0.1% TFA). Finally, the desired purified product was crystallized from 50% aqueous acetonitrile solution at 4° C. for 1 month.

EXAMPLE 3

Identification of BS-38 (Part 1)

Figure 2:
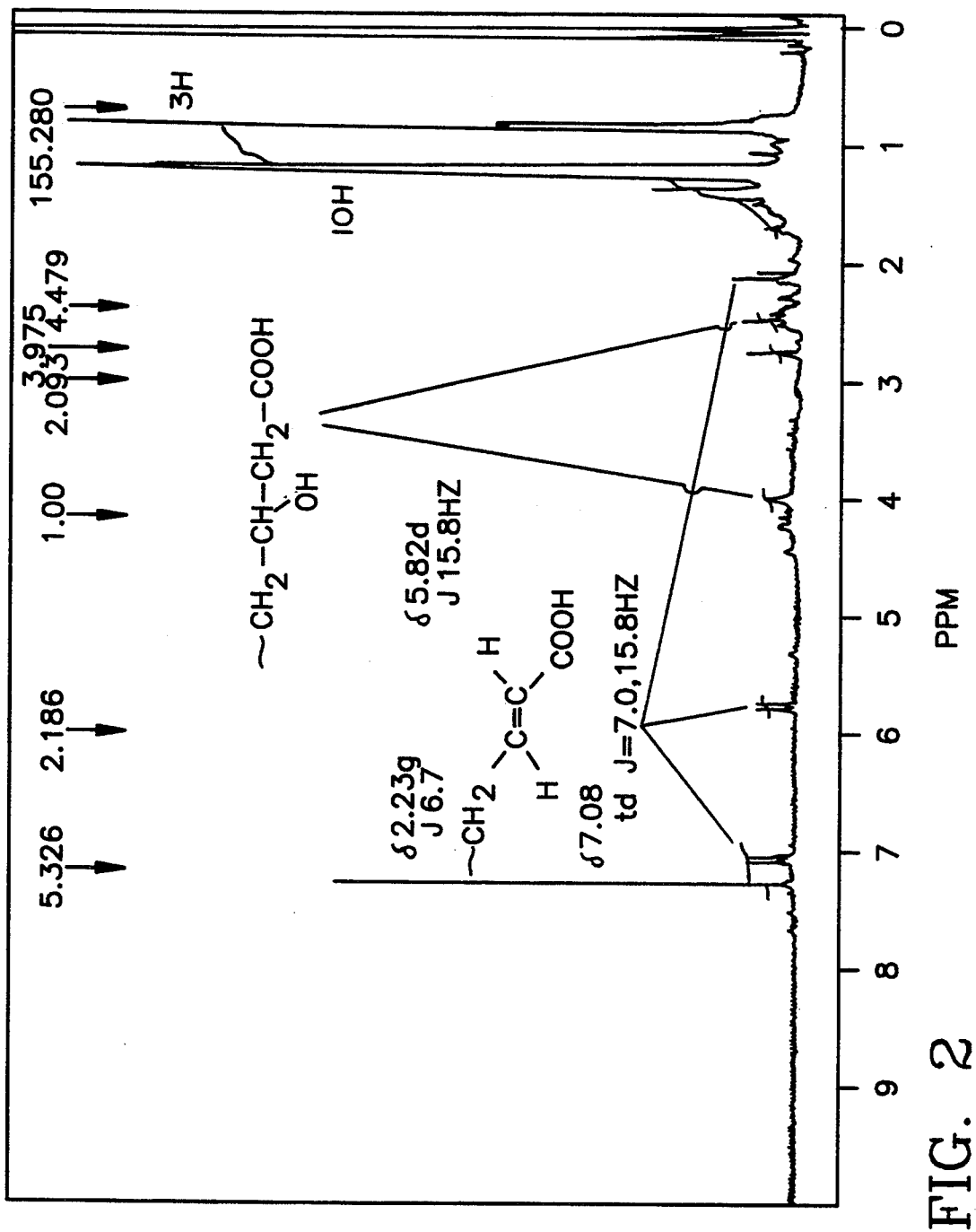
FIG. 2 shows an NMR spectrum of the fatty acid obtained by hydrolyzing the compound according to the present invention.

Infrared spectrum of BS-38 is shown in FIG. 1. Since absorption peaks are observed at 1540 cm⁻¹ and 1650 cm⁻¹, as well as at 1730 cm⁻¹ it was assumed that this compound is a peptide lipid having a lactone ring. Mass spectrometry (FAB-MS) of BS-38 revealed that the compound has a molecular weight of 1354. After hydrolyzing BS-38 with 6N HCl at 110° C. for 18 hours, the liberated fatty acid was extracted with diethyl ether and the extract was subjected to NMR (solvent: CDCl₃). The results of the NMR are shown in FIG. 2. Mass spectrometry (EI-MS) of the above-mentioned fatty acid revealed that the fatty acid has a molecular weight of 188. From these, the fatty acid was identified as having the structure represented by the formula [III] below.

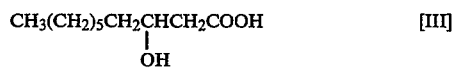

On the other hand, BS-38 was hydrolyzed with 6N HCl (containing 0.2 wt % of phenol) at 110° C. for 24 hours and its amino acid composition was determined. From the results of this amino acid analysis and from the fact that the molecular weight of the peptide moiety is 1184 (1354 - (188 - 18)), it was deduced that BS-38 contains aspartic acid, isoleucine, threonine, serine and leucine in a molar ratio of Asp:Ile:Thr:Ser:Leu=2:2:1:2:4. Further, linked scan by FAB-MS revealed that amino acids having molecular weights of (113)-115-101-113-113-87-113-87-113-113-115 are arranged in the order mentioned. The peptide was subjected to Edman degradation. From the results of the Edman degradation and the above-mentioned amino acid analysis, the amino acid sequence was determined to be leucine-aspartic acid-threonine-leucine-leucine-serine-leucine-serine-isoleucine-isoleucine-aspartic acid. From the overall results mentioned above, the structure of BS-38 was identified as represented by the above-described formula [I].

EXAMPLE 4

Identification of BS-38 (Part 2)

Figure 3:
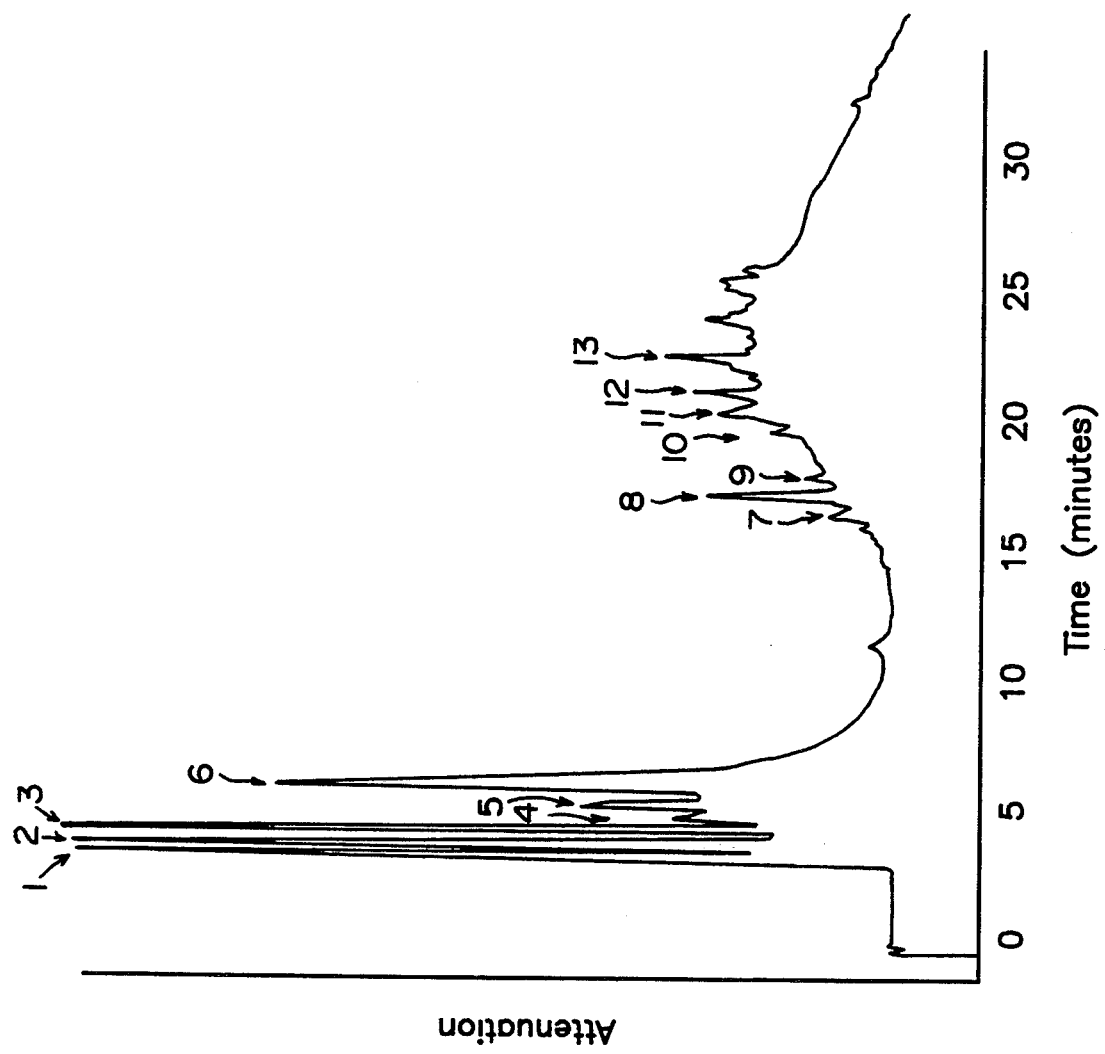
FIG. 3 shows a chromatogram obtained by subjecting the hydrolysate of the compound according to the present invention to a reverse phase chromatography.
Figure 4:
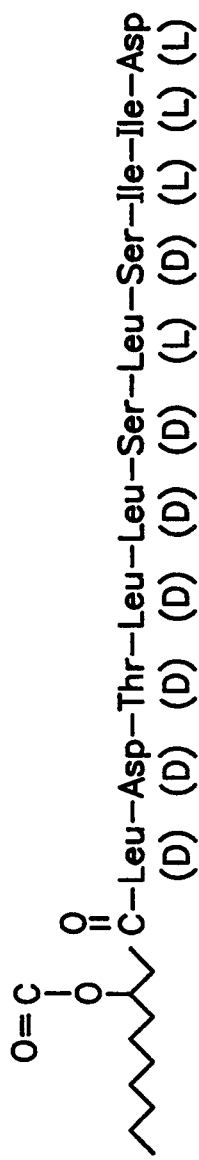
FIG. 4 shows the structure of the peptide of each peak, which was deduced by amino acid analysis of each peak shown in FIG. 3.

BS-38 was hydrolyzed with 11.5N HCl at 37° C. for 3 days. The obtained hydrolysate was subjected to reverse phase HPLC to obtain the chromatogram shown in FIG. 3. The HPLC was performed by using μBONDASPHERE (trademark) and employing linear gradient of aqueous 10 wt % AcCN (5 minutes after beginning of chromatography) to aqueous 90 wt % AcCN (35 minutes after beginning of chromatography) as an eluent. The rate of applying the eluent was 0.5 ml/min. The peptides were detected at a wavelength of 215 nm. Peaks ①to 13 shown in FIG. 3 were taken. Total volume of each peak was completely hydrolyzed and half volume of the resultant was subjected to amino acid analysis. As a result, each peak contained the peptide fragment shown in FIG. 4. These results are in commensurate with the chemical structure shown by the formula [I].

Using the remaining half volumes of the peaks ③, ⑥, ⑦, 12 and 13, the optical structure (D- or L-) of each amino acid was determined by HPLC. Optically active (+)-1-(9-fluonyl)ethylchloroformate (FLEC) (commercially available from Eka Nobel) was attached to each amino acid to obtain a diastereomer derivative, and the obtained diastereomer derivative was analyzed by a conventional method (Anal. Chem. 59, 1191–1195 (1987)). As a result, it was determined that BS-38 has the structure shown by the following formula [II].

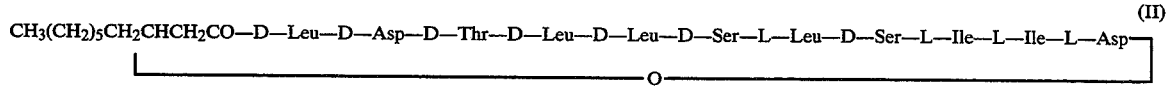

(II)

EXAMPLE 5

Surface Activity of B8-38

The surface activity of B8-38, as well as those of surfactin, Triton X-100 (trademark) and sodium dodecyl sulfate (SDS) as comparative examples, was determined by a known method (Japanese Laid-open Patent Application (Kokai) No. 5-211892). More particularly, in a petri dish having a diameter of 16 cm, 40 ml of distilled water was placed. On the water surface, 15 μl of crude oil was gently dropped to form a thin membrane of the crude oil in the entire petri dish. On the thus formed thin membrane, 10 μl of test sample was slowly placed, so as to emulsify the crude oil, thereby forming an emulsified circle. The longer diameter and the shorter diameter of the emulsified circle were measured and the area of the emulsified circle was calculated. The higher the oil-emulsifying activity, the larger the area of the emulsified circle. Thus, by comparing the areas of the emulsified circles, the oil-emulsifying activities of surfactants can be compared. Aqueous solutions of the above-mentioned surfactants diluted to various concentrations were used as the test samples.

Figure 5:
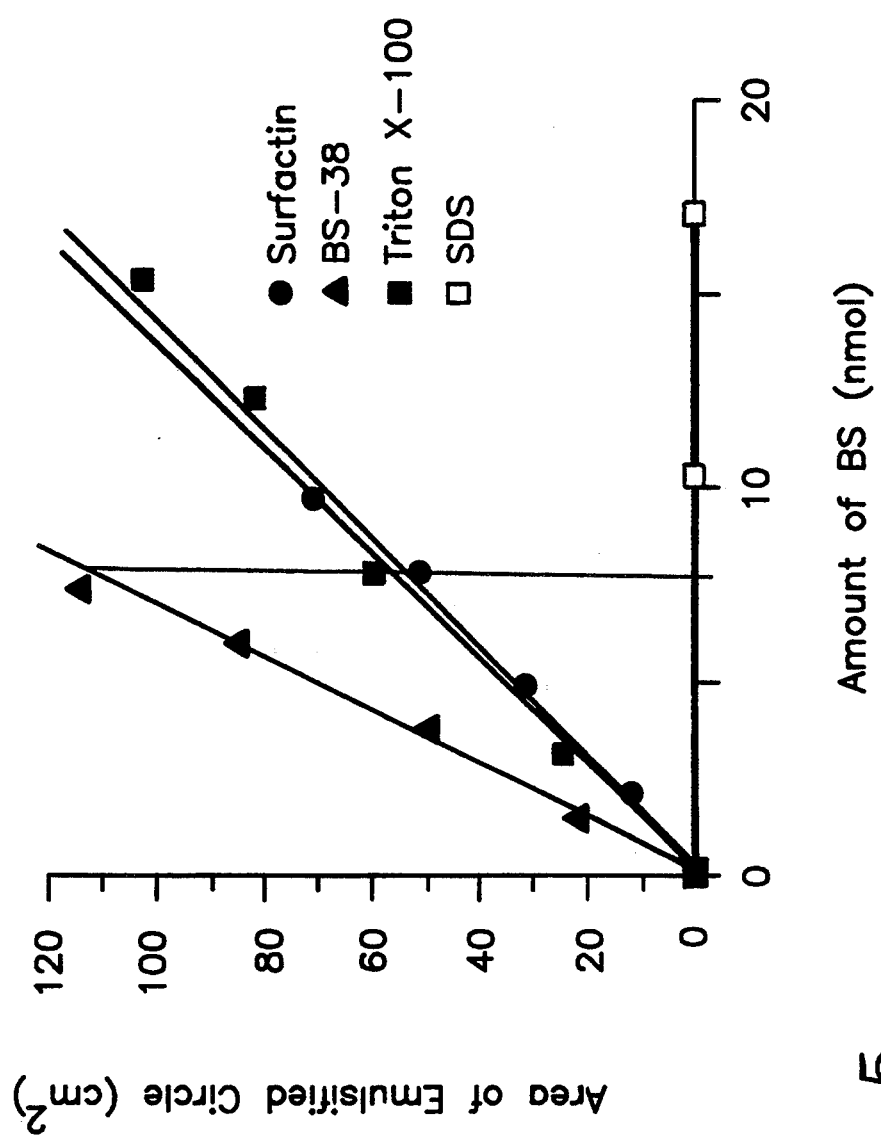
FIG. 5 shows surface activities of the compound according to the present invention and a compound of a comparative example at various concentrations.

The results are shown in FIG. 5 and Table 1 below.

TABLE 1

| Comparison of Oil-Emulsifying Activity of Surfactants | | |
|---|---|---|
| | Oil-Emulsifying Activity | |
| Surfactants | (cm$^2$/μg) | (cm$^2$/nmol) |
| BS-38 | 10.5 | 14.2 |
| Surfactin | 6.2 | 6.5 |
| Triton X-100 | 11.0 | 7.1 |
| SDS | 0.9 | 0.3 |

As can be seen from Table 1, the activity of BS-38 per a unit weight is as high as 1.7 times that of surfactin which is said to have the highest activity of all the known biosurfactants. The activity of BS-38 per a unit weight is as high as comparable to that of Triton X-100. Further, as can be seen from Table 1 and FIG. 5, the activity of surfactin per mole is comparable to that of Triton X-100, while that of BS-38 is as high as about twice that of surfactin or Triton X-100.

EXAMPLE 6 pH Dependence of Oil-Emulsifying Activity

BS-38 or surfactin was diluted with aqueous 0.5N HCl or 0.5N NaOH solution or distilled water and the oil-emulsifying activities were determined as in Example 5, thereby determining the pH dependence of the oil-emulsifying activity of the biosurfactants. The results are shown in Table 2.

TABLE 2

| pH Dependency of Oil-Emulsifying Activity | | | | |
|---|---|---|---|---|
| | | | Oil-Emulsifying Activity | |
| BS | Diluent | pH | (cm$^2$/μg) | (cm$^2$/nmol) |
| BS-38 | 0.5N HCl | 0.5 | 6.7 | 9.1 |
| | 0.5N NaOH | 13.5 | 10.0 | 13.5 |
| | Distilled Water | 8.1 | 11.0 | 14.9 |
| Surfactin | 0.5N HCl | 0.5 | 0.7 | 0.7 |
| | 0.5N NaOH | 13.5 | 8.3 | 8.6 |
| | Distilled Water | 8.1 | 6.1 | 6.3 |

As can be seen from Table 2, the activity of surfactin was drastically decreased in the acidic condition. On the other hand, although the activity of BS-38 was decreased in the acidic condition, the decrease was not so large as that of surfactin.

EXAMPLE 7

Measurement of Surface Tension

Figure 6:
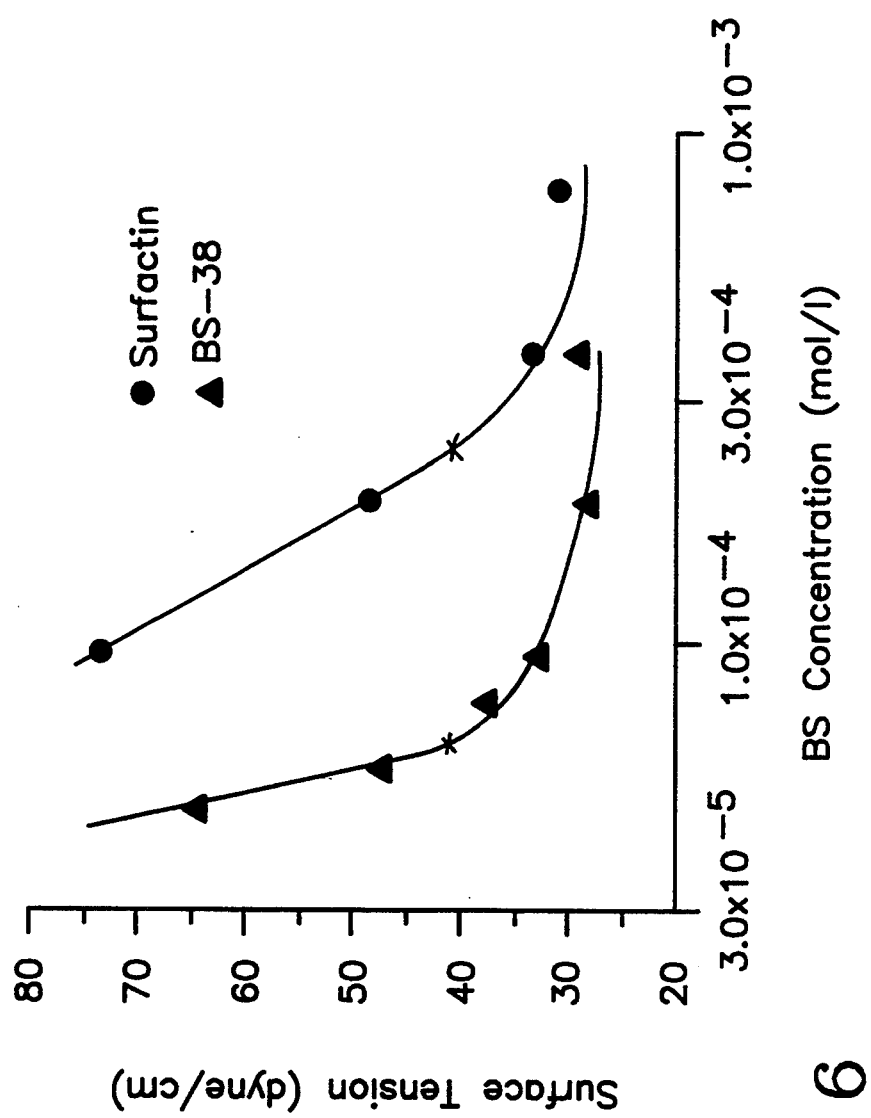
FIG. 6 shows surface tensions of the compound according to the present invention and a compound of a comparative example at various concentrations.

The surface tensions of BS-38 and surfactin were determined changing the concentration variously. The results are shown in FIG. 6. From FIG. 6, critical micelle concentration (CMC) was determined. The CMC of BS-38 was $8.0 \times 10^{-5}$ M, and that of surfactin was $3.0 \times 10^{-4}$ M.

We claim:

1. A compound represented by the formula [I].

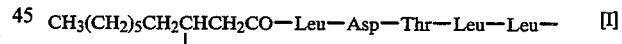

[I]

2. The compound according to claim 1, which is represented by the formula [II].

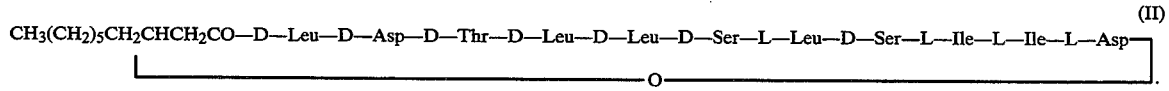

(II)

* * * * *